United States Patent [19]
Renslow

[11] Patent Number: 6,076,410
[45] Date of Patent: Jun. 20, 2000

[54] LIQUID SAMPLE COLLECTOR AND LIQUID RETURN APPARATUS

[75] Inventor: Bruce E. Renslow, Castaic, Calif.

[73] Assignee: Hanson Research Corporation, Chatsworth, Calif.

[21] Appl. No.: 09/145,317

[22] Filed: Aug. 31, 1998

[51] Int. Cl.[7] ..................................................... G01N 1/14
[52] U.S. Cl. .................................. 73/864.34; 73/863.23
[58] Field of Search ........................... 73/864.34, 864.33, 73/864.73, 864.11, 864.12, 864.22, 863.23

[56] References Cited

U.S. PATENT DOCUMENTS

| | | | |
|---|---|---|---|
| 5,780,306 | 7/1998 | Schels et al. | 73/864.33 X |
| 5,869,774 | 2/1999 | Becklund et al. | 73/864.34 |
| 5,942,440 | 8/1999 | Dooley et al. | 73/864.73 X |

*Primary Examiner*—Thomas P. Noland
*Attorney, Agent, or Firm*—Jack C. Munro

[57] ABSTRACT

A liquid sample collector and liquid return apparatus which takes the form of a first tube which has an open lower end which is to be submerged within a liquid source. This first tube is connected to a vacuum source located exteriorly of the liquid source which is to cause removal of aliquots (or samples). Mounted about a portion of the first tube is a second tube which has an open outer end which is spaced from the surface of the liquid source. This open outer end forms an annulus about the first tube. A valving arrangement is provided so that any liquid that is returned to the liquid source is returned only through the second tube.

7 Claims, 2 Drawing Sheets

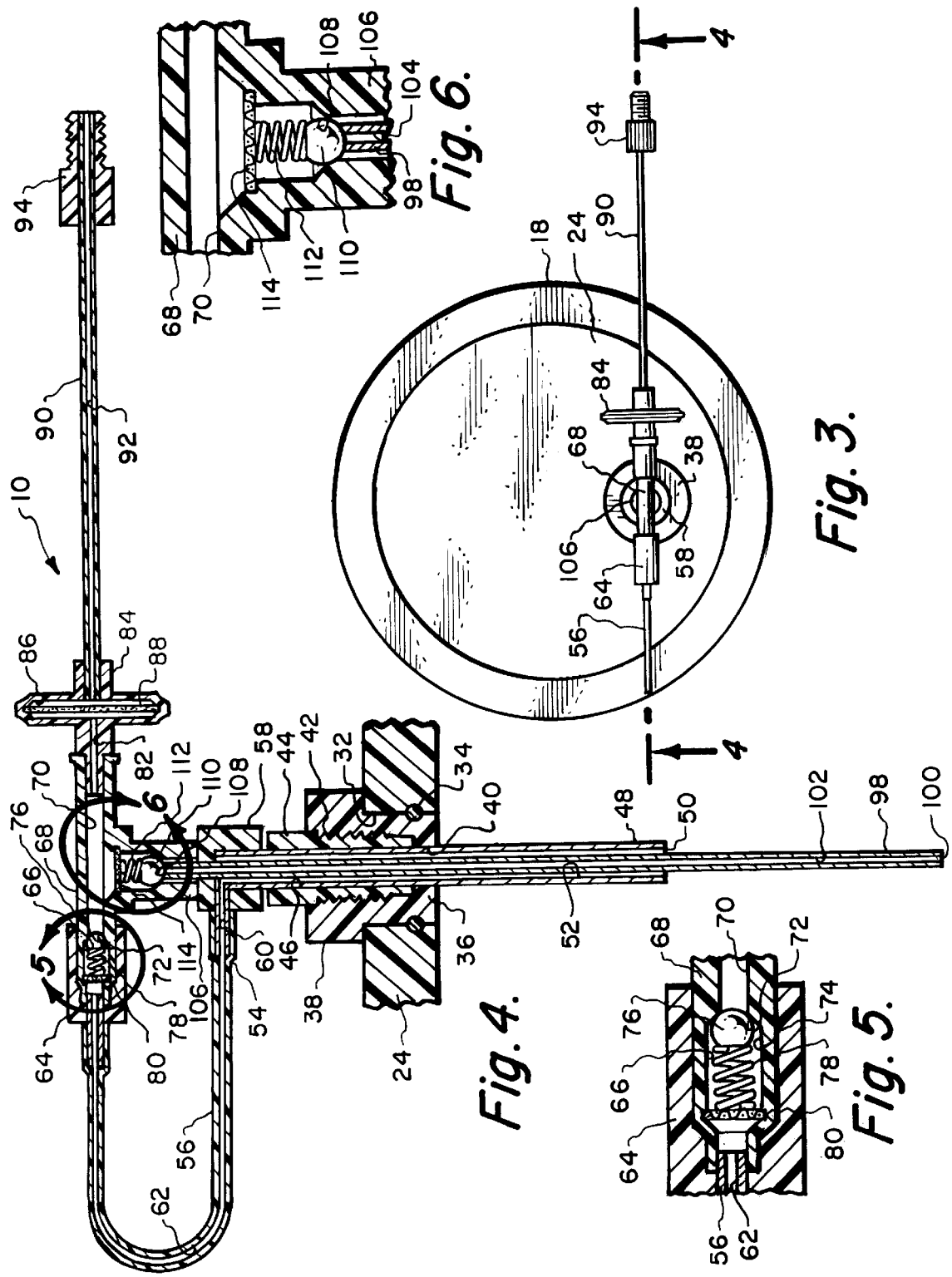

LIQUID SAMPLE COLLECTOR AND LIQUID RETURN APPARATUS

BACKGROUND OF THE INVENTION

1) Field of the Invention

The field of this invention relates to sample source interface and more particularly to a liquid sample collection device that also can be used as a sample return apparatus.

2) Description of the Prior Art

Drugs are commonly manufactured in the form of pills.

The reason for using pills is that when the drug is swallowed by a human, the drug will be disseminated into the body over a period of time as the pill dissolves. Manufacturers of pills are required by law to determine the precise dissolving characteristics of their pill before it is placed on the market. In order to determine the dissolving characteristics of pills, dissolution test equipment in the form of stations are utilized. Although dissolution test equipment is commonly used in conjunction with drugs designed for human consumption, it is considered to be within the scope of this invention to use it with other animals such as horses, cows, rabbits, cats, dogs, monkeys, and so forth.

Every known form of dissolution test equipment utilizes one or more liquid containing flasks. In each flask is to be placed a solution with that solution essentially duplicating the liquid solution that is contained within the stomach of the human body. A precise quantity of the solution is placed within the flask. The pill is then inserted within the flask with the time of the insertion then noted. A mixing paddle is mounted within the flask with mixing at a precise rate of the liquid contained within the flask then occurring. The mixing procedure is to duplicate the natural turbulence that is created within the stomach of the human. Aliquots or samples are removed from the solution at precise time intervals with these samples then being analyzed to determine the amount of the drug that has been dissolved within the solution in relation to the time the pill has been in solution.

In order to insure that this testing process is accomplished as accurately as possible, such dissolution test equipment in the past has been designed to have a plurality of flasks, such as six or eight. Dissolution testing of the pill is accomplished simultaneously in all six or eight flasks with each flask to receive a pill. The average dissolving rate is then calculated between the flasks. It is important that each flask contains precisely the identical amount of liquid. If the flask contains different volumes, inherently the dissolving rate of a pill within one flask can be significantly changed relative to another flask. Additionally, the temperature of the liquid within each of the flasks is also to be identical. It is also important to achieve the precise turbulence in each of the flasks with it being understood that if a flask encounters a greater amount of turbulence, that flask will typically have a faster dissolving rate. Therefore, it is desirable when removing of samples that such be accomplished with a minimum degree of turbulence. Also, the return of liquid to the liquid source is to be accomplished in a manner minimizing the disruption of the liquid contained within the flask.

In the past, to remove and replace samples and add liquid to a flask, there was mounted two separate tubes in conjunction with the flask. One tube was used to remove liquid and the other was used to add liquid. The disadvantages of such a system was that (1) two separate tubes were required and (2) the return tube supplied liquid to the flask in a manner that was disruptive to the liquid in the flask increasing turbulence in the flask producing inaccurate readings of the dissolution rates of the pill in the flask.

SUMMARY OF THE INVENTION

A liquid sample collector and liquid sample return apparatus which is designed to be mounted in conjunction with a lid of each flask that is utilized within dissolution test equipment. The apparatus takes the form of a mounting member which is mounted within an opening formed within the lid. The mounting member is capable of being manually adjustable to various positions so as to insure that the apparatus does not interfere with other structure associated with the lid. Fixedly mounted within the mounting structure is a first tube (collection) the lower end of which is submerged within the liquid contained within the flask. This first tube is connected through a check valve that permits only flow in the direction from the liquid, through a filter to remove any undesirable impurity, to a sample collection container. The removal of the liquid to the sample collection container is accomplished by the applying of a vacuum to the first tube. Normally, it is desirable to return a portion of the sample that is removed, and possibly after testing of the sample, the entire quantity of the sample may be returned to the liquid. Other liquids may also be delivered to the flask through this path. The sample is caused to move by pressure being applied which forces the liquid of the sample back through the filter, backwashing the filter, and then through a return line to a second tube which concentrically surrounds the first tube. The second tube is substantially shorter than the first tube with its outer end, which comprises its outlet, forming an annulus. Because the flow through the outlet is distributed by the annulus, the liquid returns to the flask with a minimum of disruption of the liquid source. A check valve is included within the return tube which permits flow of the liquid only in the direction toward the liquid source.

One of the primary advantages of the present invention is that it permits samples to be removed and returned to a liquid source through a single line eliminating the need for two separate lines.

Another objective of the present invention is to construct a liquid sample collector and liquid return apparatus which utilizes a backwash feature that reduces problems associated with absorption of the sample onto the filter and cleans the conduit path reducing a problem associated with residual liquid contained within the conduit path.

Another objective of the present invention is to provide a liquid sample collector and liquid return apparatus which returns the sample to the liquid in a manner with minimal disrupting of the liquid thereby minimally affecting the sample status.

BRIEF DESCRIPTION OF THE DRAWINGS

FIG. 3 is a top plan view of the liquid sample collector and liquid return apparatus of the present invention taken along line 3—3 of FIG. 2;

FIG. 4 is a cross-sectional view of the mechanism utilized within the liquid sample collector and liquid return apparatus of the present invention taken along line 4—4 of FIG. 3;

FIG. 5 is an enlarged view of the check valve utilized in conjunction with the return flow path of the liquid sample collector and liquid return apparatus of the present invention taken along line 5 of FIG. 4; and FIG. 6 is an enlarged view of the check valve that is utilized in conjunction with the discharge flow path of the liquid sample collector and liquid return apparatus of the present invention taken along line 6 of FIG. 4.

DETAILED DESCRIPTION OF THE PREFERRED EMBODIMENT

Figure 1:
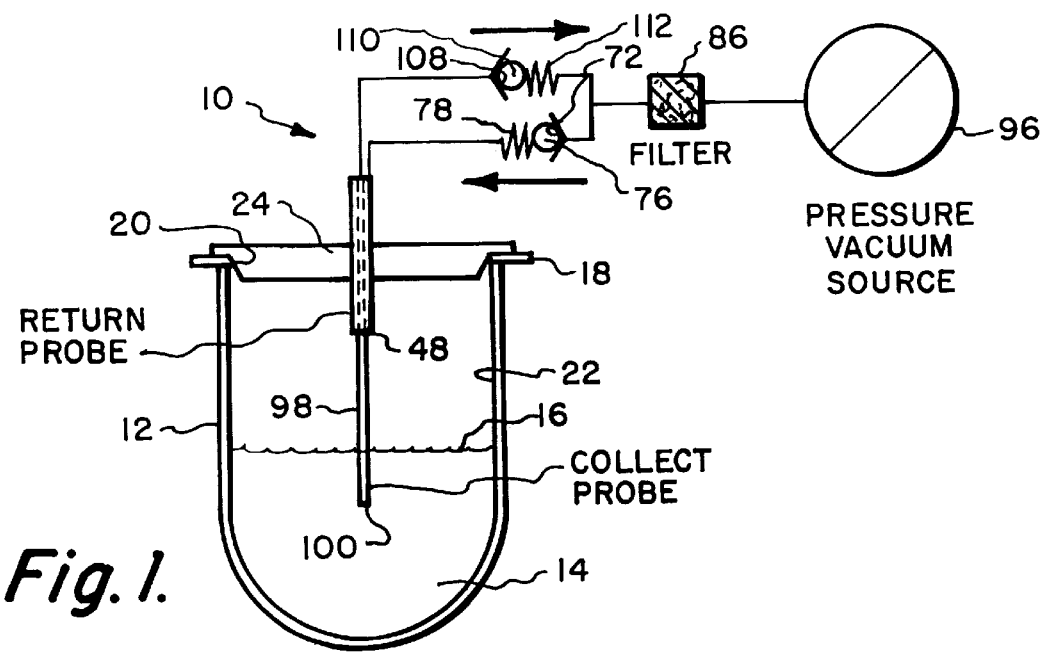
FIG. 1 is an overall schematic view of the liquid sample collector and liquid return apparatus of the present invention.
Figure 2:
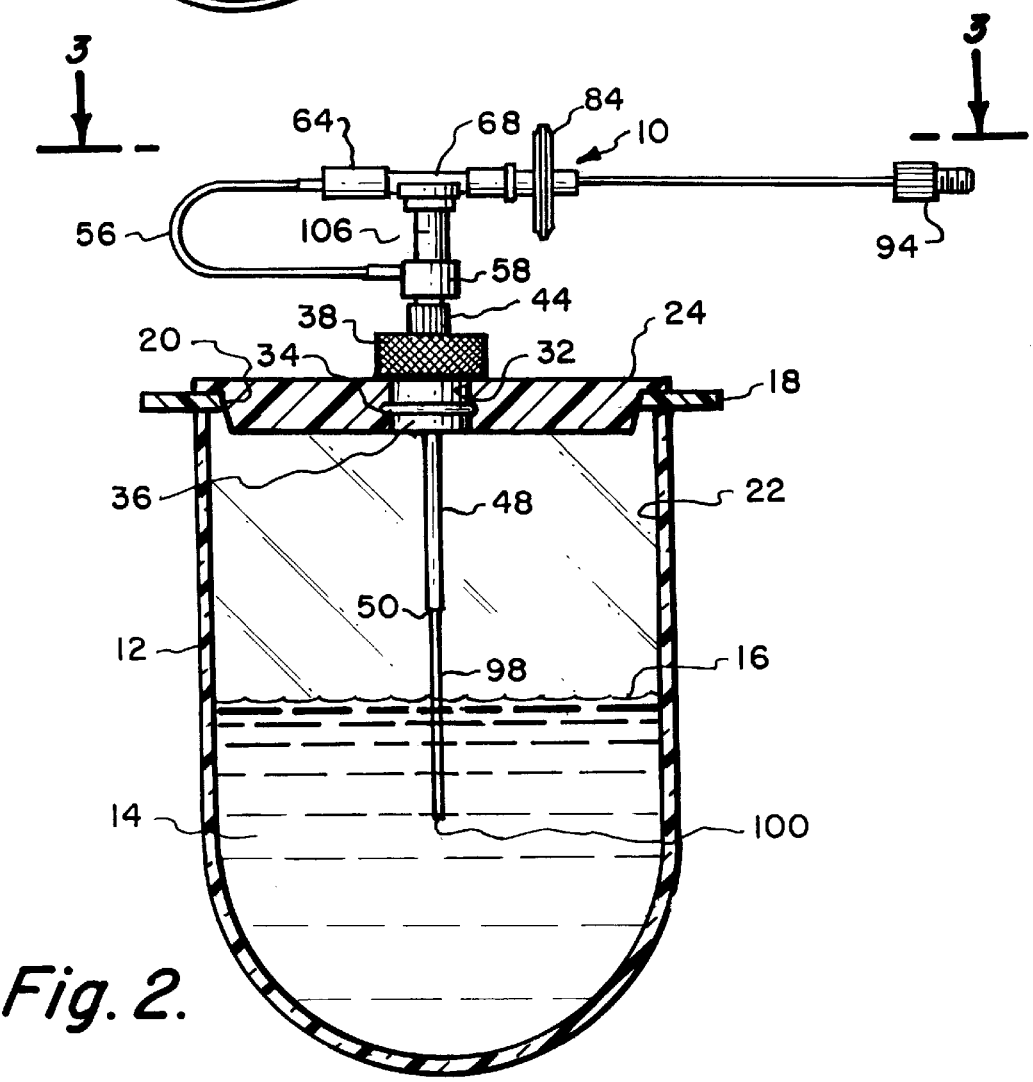
FIG. 2 is a cross-sectional view of the actual liquid sample collector and liquid return apparatus of the present invention.

Referring particularly to the drawings, there is shown the liquid sample collector and liquid return apparatus 10 of this invention. Apparatus 10 is intended to be used in conjunction with a vessel or flask 12. The flask 12 usually contains a special composition of liquid 14 with a typical liquid being a mild form of hydrochloric acid. The liquid 14 has a surface 16. The flask 12 normally is constructed of a transparent material such as glass or plastic.

The flask 12 includes an annular flange 18 which is located around the access opening 20 providing access into the internal chamber 22 of the flask 12. Within the internal chamber 22 is to be located the liquid 14. Mounted within the access opening 20 and substantially closing such is a lid 24. This lid 24 is normally constructed of a rigid plastic and is designed to prevent sample evaporation and is readily removable from the access opening 20 in order to gain access into internal chamber 22, for example, when it is desired to clean the flask 12.

The lid 24 includes a through hole 32. Mounted within the through hole 32 is an O-ring seal 34. Locatable within the through hole 32 is a mounting plug 36. The mounting plug 36 is merely to rest within the through hole 32 and is capable of being manually pivoted relative to the lid 24. The purpose of this pivoting is to provide adjustability of the locating position of the apparatus 10 of this invention. The purpose of the O-ring seal 34 is to cause a tight frictional fit to prevent free rotation of the mounting plug 36 relative to the lid 24.

The mounting plug 36 has an enlarged head 38 which is knurled on its exterior surface facilitating manual grasping and turning movement of the mounting plug 36. The mounting plug 36 and the enlarged head 38 have a through hole 40 part of which includes a series of internal threads 42. A sleeve 44 is threadably connected with the internal threads 42. The sleeve 44 has a center through hole 46. Tightly mounted within the center through hole 46 is a tube 48 with this tube 48 having an outer open end 50 which connects with a through passage 52. The upper end of the through passage 52 connects with a conduit 54 which connects with a flexible tube 56. Conduit 54 is formed within sleeve 58. The sleeve 58 is fixedly mounted on the tube 48. The through passage 52 connects with the passage 60 formed within the conduit 54. The passage 60 connects with through passage 52 formed within the flexible tube 56.

Flexible tube 56 is also mounted on a return valve housing 64. Return valve housing 64 has a through hole 66 within which is mounted one end of a conduit 68. The conduit 68 includes a through passage 70 which terminates at one end in a valve seat 72. The valve seat 72 connects with enlarged chamber 74 within which is mounted a ball 76 and a spring 78. One end of the spring 78 abuts against the ball 76 with the opposite end of the spring 78 abutting against a spring retainer 80. Spring retainer 80 is in the form of a screen which is capable of readily passing liquid therethrough. Normally the bias of the spring 78 is to position the ball 76 against the seat 72 preventing the passage of flow of liquid 14 from through passage 70 into the through passage 62.

The passage 70 connects with a passage 82 of a filter housing 84. Conduit 68 is tightly mounted onto the filter housing 84. The filter housing 84 includes an enlarged filter chamber 86 within which is located a filter 88. The filter 88 is capable of trapping exceedingly small, solid particles that may be contained within the liquid 14. The filter housing 84 is also connected to a discharge/return tube 90. Contained within the discharge/return tube 90 is a through passage 92. The through passage 92 connects with the passage 82.

The discharge/return tube 90 connects to a connector 94. The connector 94 is designed to be connected to a pressure/vacuum source 96. The pressure/vacuum source 96 also includes some type of a sample collection container which is not specifically shown.

Mounted within the through passage 52 is a tube 98. The tube 98 has a lower end 100 which comprises the free end of the tube 98. The tube 98 includes a through passage 102. The tube 98 is mounted within the through passage 52 of the tube 48. The result is the through passage 52 assumes an annular configuration, the purpose of which will be explained further on the specification. The tube 98 is mounted within the sleeve 58 with the passage 102 connecting with a chamber 104 formed within a valve housing 106. Mounted within the chamber 104 is a valve seat 108 with a ball 110 normally resting on the seat 108. The ball 110 engages with one end of a coil spring 112 with the opposite end of the coil spring 112 engaging with a screen spring retainer 114. The chamber 104 connects directly with the through passage 70.

The operation of the liquid sample collection and liquid return apparatus 10 of this invention is as follows: The mounting plug 36 is installed within the through hole 32 with the enlarged head 38 being pivoted to the desired angular position so as to not interfere with any exterior structure. The connector 94 is then connected to the pressure vacuum source 96. The pressure vacuum source 96 is to be connected to a collecting container which could take any of numerous forms such as a collection carousel that is used for analysis of the sample (or aliquot) that has been deposited within the container. Initially, a vacuum is applied within the through passage 92. This vacuum is also applied to the passage 82 and passage 70. The vacuum is not appliable within the through passage 62 since the ball 76 is seated and actually the application of vacuum further aids the tightly seating of the ball 76. However, the ball 110 is caused to be unseated slightly compressing of the coil spring 112. This permits the vacuum to be applied into chamber 104 and into the through passage 102. Since the lower end 100 of the tube 98 is submerged, about midway of the depth of the liquid 14, liquid 14 is drawn into the passage 102, into chamber 104, past the ball 110, through the screen 114, into passage 70 and then through the passages 82 and 92 to the collecting container that is associated with the pressure vacuum source 96. When the desired amount of sample has been collected, pressure is then applied at the pressure vacuum source 96 which forces a portion of this sample in the reverse direction. This will cause a backwashing of the filter 88. This pressure causes the ball 110 to be tightly seated against the seat 108 preventing the flow of fluid from passage 70 into the chamber 104. However, this pressure will cause the ball 76 to be unseated which will cause the liquid 14 to flow into through passage 62, into passage 52 and then back into the liquid 14 by being deposited from outer open end 50. Because this depositing is occurring from an annulus, there is a tendency for the liquid 14 to be conducted along the outer surface of the tube 98 due to capillary action. It is to be noted that the outer open end 50 is spaced above the surface 16 of the liquid 14. It is desirable to return the liquid 14 above the surface 16 in a manner to minimally affect the dissolution rate of the pill within the liquid 14 maintaining sample integrity. Also, because the liquid that is being returned to the liquid 14 is flowing along the outer surface of the tube 98 due to capillary action, disruption of the liquid 14 is minimal.

One of the most desirable features of the present invention is that a single line is, in essence, being used for removal of the sample liquid 14 and also return of that same sample, or a portion of that sample to the liquid 14, eliminating the need for two separate lines which is commonly used within the prior art. The single line can be used to collect a liquid sample from a liquid source, return all or part of the sample to the source, replace liquid to the source, or add additional ingredients to the source such as a pH buffer.

What is claimed is:

1. A liquid sample collector and liquid return apparatus comprising:

a first tube having an open lower end, said lower end adapted to be submerged within a first liquid source, said first tube having an upper end, said upper end being connected to a discharge tube, said discharge tube adapted to connect to a vacuum source in order to cause liquid to flow through said first tube and said discharge tube to be supplied into a sample collection container;

a second tube having an open outer end, said outer end adapted to be located directly adjacent a second liquid source, said second tube having an inner end, said inner end being connected to a return tube, said return tube adapted to connect to a third liquid source which is pressurized to cause at least a portion of said third liquid source to flow through said return tube and said second tube to said second liquid source; and said first tube being mounted within said second tube.

2. The liquid sample collector and liquid return apparatus as defined in claim 1 wherein:

a filter being connected within said discharge tube and said return tube.

3. The liquid sample collector and liquid return apparatus as defined in claim 1 wherein:

said first tube being longer than said second tube so said second tube does not submerge within said first liquid source.

4. The liquid sample collector and liquid return apparatus as defined in claim 1 wherein:

said second tube being concentric to said first tube, whereby the configuration of said outer end of said second tube being that of an annulus about said first tube.

5. The liquid sample collector and liquid return apparatus as defined in claim 1 wherein:

said discharge tube including a first check valve, said return tube including a second check valve, whereby said first check valve permits flow of liquid from said first liquid source and said second check valve permits flow of liquid only toward said second liquid source.

6. The liquid sample collector and liquid return apparatus as defined in claim 1 wherein:

said first liquid source and said second liquid source comprising a single liquid source.

7. The liquid sample collector and liquid return apparatus as defined in claim 1 wherein:

said first tube and said second tube being fixedly mounted within a mounting device, said mounting device being mounted within a lid for a flask, said mounting device being adjustable to different positions relative to said lid.

* * * * *